United States Patent [19]

Sotoya et al.

[11] Patent Number: 5,220,051
[45] Date of Patent: Jun. 15, 1993

[54] POLYCATIONIC COMPOUND AND BLEACH COMPOSITION CONTAINING THE SAME

[75] Inventors: Kohshiro Sotoya; Nobuyuki Ogura; Hiroyuki Imoto, all of Wakayama, Japan

[73] Assignee: KAO Corporation, Tokyo, Japan

[21] Appl. No.: 604,525

[22] Filed: Oct. 29, 1990

[30] Foreign Application Priority Data

Nov. 8, 1989 [JP] Japan .................... 1-290315
Aug. 2, 1990 [JP] Japan .................... 2-206396

[51] Int. Cl.$^5$ .................... C07C 69/00; C09K 3/00
[52] U.S. Cl. .................... 560/142; 252/186.38
[58] Field of Search .................... 560/142; 252/186.38

[56] References Cited

U.S. PATENT DOCUMENTS

| | | | |
|---|---|---|---|
| 3,650,749 | 3/1972 | Willems et al. | 430/564 |
| 4,026,708 | 5/1977 | Vanassche et al. | 430/566 |
| 4,279,769 | 7/1981 | Yagi et al. | 252/186 |
| 4,904,406 | 2/1990 | Darwent et al. | 252/102 X |
| 4,933,103 | 6/1990 | Aoyagi et al. | 252/186.38 X |
| 5,093,022 | 3/1992 | Sotoya et al. | 252/102 X |

FOREIGN PATENT DOCUMENTS

| | | | |
|---|---|---|---|
| 1929223 | 12/1969 | Fed. Rep. of Germany | 430/564 |
| 2506350 | 9/1975 | Fed. Rep. of Germany | 430/566 |

OTHER PUBLICATIONS

CA 99(24):196972e "Synthesis and some surface active properties of alpha.omega.-type amphoteric surfactants. Gama, Yasuo" Japan.
CA114(10):85132q Composition for suppressing swelling of clays in flooding of oil-bearing formations. Ivashov, Russia 1990.
Chem. Ab. vol. 108, No. 15, Apr. 11, 1988, Columbus, Oh., F. Devinsky et al.
European Search Report.

*Primary Examiner*—Richard D. Lovering
*Assistant Examiner*—Joseph D. Anthony
*Attorney, Agent, or Firm*—Birch, Stewart, Kolasch & Birch

[57] ABSTRACT

The polycationic compound having the formula (I) is useful for an organic peracid precursor. A bleach composition comprises the polycationic compound and a peroxide.

$$Z_m - X - [Y - X]_n - Y - X - Z_{m'} \cdot (n + 2)A \quad (I)$$
$$\overset{|}{Z_{m-1}}$$

in which X is a cation, Y is an alkylene, Z is a specific group containing carbonyl group and A is an anionic group.

4 Claims, No Drawings

POLYCATIONIC COMPOUND AND BLEACH COMPOSITION CONTAINING THE SAME

The present invention relates to a polycationic compound which can react with hydrogen peroxide to give an organic peracid, thus being useful as an organic peracid precursor, and to a bleach composition containing the same.

PRIOR ART

A chlorinated bleaching agent has significant disadvantages in that the fibers to which it is applicable are limited, in that it is not applicable to colored or patterned cloths, and in that it has a peculiar odor, though it exhibits a very high bleaching effect.

Therefore, an oxygenic bleaching agent free from these disadvantages has recently been used widely.

As such an oxygenic bleaching agent, sodium percarbonate and sodium perborate are particularly preferably utilized from the standpoint of bleaching performance and storage stability.

Although the oxygenic bleaching agent is applicable to colored or patterned cloths, unlike chlorinated bleaching agents, the bleaching power thereof is so poor that the use of various bleach activators, which are convertible into an organic peracid having a higher oxidation-reduction potential, has been attempted. For example, studies have been made on various bleach activators including nitriles such as acetonitrile, malononitrile, phthalonitrile and benzoyliminodiacetonitrile; O-acetyl compounds such as glucose pentaacetate, octaacetylsucrose, triacetin, sorbitol hexaacetate, acetoxybenzenesulfonate salt, triacetyl cyanurate and methyl chloroformate; N-acetyl compounds such as N,N,N',N'-tetraacetylethylenediamine, tetraacetylglycoluril, N-benzoylimidazole, di-n-acetyldimethylglyoxime, 1-phenyl-3-acetylhydantoin, N,N-diacetylaniline, N-acetyldiglycolimide and diacetylmethylenediformamide; acid anhydrides such as phthalic, succinic, benzoic, glutaric and alkylsulfuric anhydrides and mixed anhydrides of carboxylic acids with organosulfonic acids; sulfonyl oximes such di(methanesulfonyl)dimethylglyoxime acylated phosphate salts such as diethylbenzoyl phosphate salts; phenyl sulfonate esters; organophosphoric acid azides such as diphenylphosphinic azide; disulfones such as diphenyl disulfone; N-sulfonylimidazole; cyanamides; halogenated triazines and N,N-dimethyl-N-octyl-N-10-carbophenoxydodecylammonium chloride. However, the bleaching power is still insufficient even if such a bleach activator is used simultaneously.

DISCLOSURE OF THE INVENTION

The inventors of the present invention have intensively studied to obtain a higher-performance oxygenic bleaching agent and have found that when a peroxide and a polyamine derivative as an organic peracid precursor are used simultaneously, the formed organic peracid is concentrated on the surface of the cloth to give a remarkably enhanced bleaching effect. The present invention has been accomplished on the basis of this finding.

Namely, the present invention provides a new polycationic compound useful as an organic peracid precursor and represented by the following general formula (I), and a bleach composition comprising a peroxide and said polycationic compound:

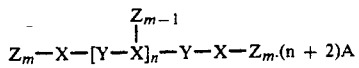

wherein

X: an $N^+$, $S^+$ or $P^+$ cationic group, wherein a plurality of X groups may be the same or different from each other, Y: an alkylene group having 1 to 9 carbon atoms, which may be substituted with a hydroxyl group or a $-(C_2H_4O)_{1\sim 5}-C_2H_4-$ or $-(C_3H_6)_{1\sim 5}-C_3H_6-$ group, wherein a plurality of Y groups may be the same or different from each other,

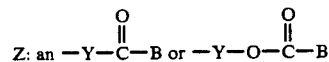

group (wherein B will be defined below), an alkyl group having 1 to 20 carbon atoms or an alkenyl group, each of which may be substituted with a hydroxyl group or a $-(C_2H_4O)_{1\sim 5}-H$ or $-(C_3H_6O)_{1\sim 5}-H$ group, with the proviso that at least one Z group is a

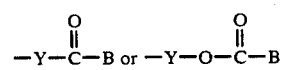

group, though the Z groups may be the same or different from each other, m: when X is $N^+$ or $P^+$, m is 3 with respect to the $Z_m$ or $Z_{m-1}$ groups bonded to the X group, while when X is $S^+$, m is 2 with respect to the $Z_m$ or $Z_{m-1}$ groups bonded to the group X, n: a number of 0 to 3, A: an inorganic or organic anionic group, with the proviso that A is absent when Z and X are combined together to form an inner salt, wherein a plurality of A groups may be the same of different from each other, wherein a plurality of the above B groups each represent any of the following groups and may be the same or different from each other in one molecule:

a)

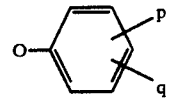

wherein p and q each represent $-H$, $-SO_3M$, $-COOM$, $COOR'$, $-OH$, a halogen atom, $-OR^1$, $-R^1$ or $-N(R^1)\cdot A$, wherein M represents an alkali metal, an alkaline earth metal, an ammonium, an alkanolammonium or a negative charge itself; $R^1$ represents H, an alkyl group having 1 to 20 carbon atoms, an alkenyl or hydroxyalkyl group or a $-(C_2H_4O)_{1\sim 5}-H$ or $-(C_3H_6O)_{1\sim 5}-H$ group; A is as defined above and p and q may be the same or different from each other, b) an oxime group having a structure represented by the formula:

$$-ON=C\begin{matrix}R^2\\\\R^3\end{matrix}$$

wherein $R^2$ and $R^3$ are the same as those defined above with respect to $R^1$ and may be the same or different from each other, with the proviso that at least one of $R^2$ and $R^3$ must not be H, c) an imidoxime group represented by the formula:

$$-ON\begin{matrix}\overset{O}{\overset{\|}{C}}-R^1\\\\\overset{\|}{\underset{O}{C}}-R^1\end{matrix}\ ,\ -ON\begin{matrix}\overset{O}{\overset{\|}{C}}\\\\\overset{\|}{\underset{O}{C}}\end{matrix}\!\!Y\ \text{or}\ -ON\begin{matrix}\overset{O}{\overset{\|}{C}}\\\\\overset{\|}{\underset{O}{C}}\end{matrix}\!\!\bigcirc$$

wherein $R^1$ and Y are as defined above, d) an alkanesulfonic acid group represented by the formula:

$$-O-Y-SO_3M$$

wherein Y and M are as defined above, e) a polyglycolic ester group represented by the formula:

$$-O(CH_2COO)_kH$$

wherein k is a number of 1 to 10, f) an acid anhydride group represented by the formula:

$$-O-\overset{O}{\overset{\|}{C}}-R^4$$

wherein $R^4$ represents an alkyl group having 1 to 22 carbon atoms, an alkenyl group or a phenyl group which may be substitute, g) an imide group represented by the formula:

$$-N\begin{matrix}\overset{O}{\overset{\|}{C}}-R^1\\\\\overset{\|}{\underset{O}{C}}-R^1\end{matrix}\ ,\ -N\begin{matrix}\overset{O}{\overset{\|}{C}}\\\\\overset{\|}{\underset{O}{C}}\end{matrix}\!\!Y\ -N\begin{matrix}\overset{O}{\overset{\|}{C}}\\\\\overset{\|}{\underset{O}{C}}\end{matrix}\!\!\bigcirc\ \text{or}$$

$$-\overset{R^1}{\underset{}{N}}-\overset{O}{\overset{\|}{C}}-R^1$$

wherein $R^1$ and Y are as defined above, h) a pyrrolidonecarboxylic acid derivative group represented by the formula:

[pyrrolidone structures with $COOR^5$ substituent]

wherein $R^5$ is the same as that defined above with respect to $R^1$ or M, i) a ketone derivative group represented by the formula:

$$-\overset{R^1}{\underset{}{\overset{|}{C}}}\begin{matrix}W\\\\W\end{matrix}$$

wherein $R^1$ is as defined above and W is $$-\overset{O}{\overset{\|}{C}}OR^1,\ -\overset{O}{\overset{\|}{C}}N(R^1)_2,\ -\overset{O}{\overset{\|}{C}}-R^1,\ -C\equiv N,$$

$$-NO_2\ \text{or}\ -SO_2R^1,$$

wherein a plurality of W groups may be the same or different from each other, or j) an enol derivative group represented by the formula:

$$-O-\overset{R^6}{\underset{}{\overset{|}{C}}}=CHR^1\ \text{or}\ -OC\begin{matrix}CH-CH_2\\\\CH_2\\\\CH_2-CH_2\end{matrix}$$

wherein $R^6$ is the same as that defined above with respect to $R^1$ excepting H.

The bleach composition of the present invention contains a polycationic compound represented by the above general formula (I) as an organic peracid precursor. This polycationic compound reacts with a peracid anion generated from a peracid in water to give an organic peracid having a plurality of positive charges in one molecule. This organic peracid is highly efficiently concentrated on the surface of a cloth, and exhibits a bleaching power dramatically improved as compared with that of the organic peracid of the prior art.

The peroxide, which can generate a peracid anion reactive with the organic peracid precursor according to the present invention, is preferably hydrogen peroxide, or a peroxide which can generate hydrogen peroxide in an aqueous solution.

Examples of a peroxide which can generate hydrogen peroxide in an aqueous solution include organic and inorganic hydrogen peroxide adducts such as sodium carbonate/hydrogen peroxide adduct, sodium tripolyphosphate/hydrogen peroxide adduct, sodium pyrophosphate/hydrogen peroxide adduct, and $4Na_2SO_4\cdot2\text{-}H_2O_2\cdot NaCl$; and inorganic peroxides such as sodium perborate monohydrate, sodium perborate tetrahydrate, sodium peroxide and potassium peroxide, among which sodium carbonate/hydrogen peroxide adduct, sodium perborate monohydrate and sodium perborate tetrahydrate are preferable.

In the bleach composition of the present invention, the peroxide and the organic peracid precursor are used in a molar ratio ranging from 99.9 : 0.1 to 20 : 80, preferably from 95 : 5 to 50 : 50. If the amount of the organic peracid precursor is below this range, only an insufficient effect will be attained, while even if the precursor is used in an amount above this range, the precursor will not act effectively, resulting in undesirable waste.

The bleach composition of the present invention may contain known additives that are conventionally added to bleach compositions, in addition to the essential components described above. Examples of such additive include water-soluble inorganic builders such as sulfates, carbonates, bicarbonates, silicates and phosphates; and organic builders such as ethylenediamine-tetraacetate salts, tartrate salts and citrate salts. If necessary, the composition of the present invention may further contain an antiredeposition agent such as carboxymethylcellulose, polyvinylpyrrolidone or polyethylene glycol, and may contain various surfactants, enzymes fluorescent whitening agents, dyes, pigments or perfumes.

Further, a bleaching detergent composition can also be prepared by suitably blending a conventional powdered detergent for cloth with the organic peracid precursor and peroxide according to the present invention.

EFFECT OF THE INVENTION

The bleach composition of the present invention characterized by containing the new polycationic compound exhibits a high bleaching power which cannot be attained by the oxygenic bleaching agents of the prior art including organic peracids.

EXAMPLE

The present invention will now be described by referring to the following Examples, though the present invention is not limited to them.

Referential Example 1 . . . synthesis of compound (1)

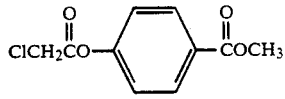
(1)

100 g of methyl p-hydroxybenzoate (MW: 152 15 0.66 mol), 300 g of acetone and 66.5 g of triethylamine (MW: 101.2, 0.66 mol) were mixed together in a 1-( four-necked flask fitted with a condenser, a mechanical stirrer and a thermometer. 77.9 g of chloroacetyl chloride (MW: 112.9, 0.69 mol) was dropped into the flask over a period of about one hour, while keeping the flask on a water bath. The reaction mixture was aged for about 2 to 3 hours. Thereafter, the triethylamine hydrochloride thus precipitated was filtered away and the acetone was distilled off under a reduced pressure. The obtained residue was further distilled under the conditions of 0.5 mmHg and 145 to 155° C to give 144.8 g of the compound (1) represented by the above formula as a white solid.

MW: 228.6, yield: 70%, purity: 92% IR (KBr cm$^{-1}$): 1776, 1722, 1605, 1503, 1284, 1200, 1161, 1110, 768

Referential Example 2 . . . synthesis of compound (2)

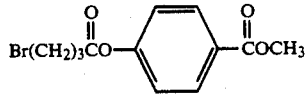
(2)

The same procedure as that of Referential Example 1 was repeated except that 122.5 g of bromobutyroyl chloride (MW: 185.6, 0.66 mol) was used instead of the chloroacetyl chloride. Thus, the compound (2) was obtained.

amount: 171.1 g, MW: 301.3, yield: 80%, purity: 93%

IR (KBr cm$^-$): 1752, 1731, 1608, 1506, 1278, 1197, 1140, 1110

Referential Example 3 . . . synthesis of compound (3)

(3)

100 g of acetoxime (MW: 73.10, 1.37 mol), 150 g of tetrahydrofuran and 108.4 g of pyridine (MW: 79.1, 1.37 mol) were mixed together in a 1-l four-necked flask fitted with a condenser, a mechanical stirrer and a thermometer. 154.7 g of chloroacetyl chloride (MW: 112.9, 1.37 mol) was dropped into the flask over a period of about one hour, while keeping the flask on a water bath. The reaction mixture was aged for about 2 to 3 hours. The pyridine hydrochloride thus precipitated was filtered away and the tetrahydrofuran was distilled off. Thus, 149.5 g of the compound (3) was obtained.

MW: 149.5, yield: 90%, purity: 90%

IR (KBr cm $^{-1}$): 3000, 2960, 2920, 1776, 1644, 1436, 1414, 1374, 1310, 1282, 1236, 1144, 1066, 928, 876, 784

Referential Example 4 . . . synthesis of compound (4)

(4)

100 g of succinimide (MW: 99, 1.01 mol), 150 g of dichloroethane and 114.0 g of chloroacetyl chloride (MW: 112.9, 1.01 mol) were placed in a 1-l four-necked flask fitted with a condenser, a mechanical stirrer and a nitrogen gas inlet tube and the temperature of the contents was raised to 80° to 85° C. under stirring. The reaction was carried out for about 5 to 10 hours, while removing the HCl gas, generated as a by-product, by introducing nitrogen into the flask. After the completion of the reaction, the disappearance of succinimide was confirmed by TLC and thereafter, the dichloroethane was distilled off. Thus, 152.7 g of the compound (4) was obtained.

yield: 75%, purity: 87%, MW: 175.4

IR (KBr cm $^{-1}$): 1812, 1755, 1713, 1635

Referential Example 5 . . . synthesis of compound (5)

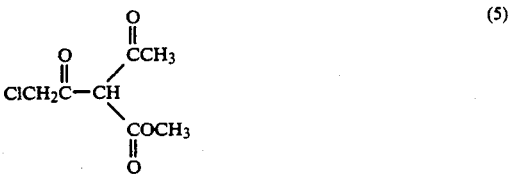
(5)

The compound (5) was prepared according to a variation of the method described in Ber., 67B, 935 (1934).

5.33 g (0.22 mol) of magnesium was placed in a 0.5-l four-necked flask, followed by the addition of 5 ml of absolute ethanol and 0.5 ml of carbon tetrachloride. After 2 or 3 minutes, 75 ml of absolute ethanol was carefully added thereto. Then, a mixture comprising 22.5 g of methyl acetoacetate (MW: 116.12, 0.22 mol), 25 ml of absolute ethanol and 25 ml of anhydrous ether was dropped into the flask, while heating the contents so as to reflux them mildly. The reaction mixture was aged for 3 hours and thereafter, 22.6 g of chloroacetyl chloride (MW: 112.9, 0.20 mol) was dropped into the flask over a period of about 30 minutes. The reaction mixture was again aged for 30 minutes and adjusted to pH 7 with 20% $H_2SO_4$. The obtained ethereal layer was washed with water and freed from the ether by distillation. Thus, 34.1 g of the compound (5) was obtained.

yield: 52.0%, purity: 76%, MW: 226.3

IR (KBr $cm^{-1}$): 2926, 2854, 1737, 1683, 1614, 1464, 1419, 1374, 1296, 1101, 774

Referential 6 . . . synthesis of compound (6)

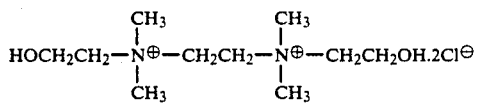
(6)

116 g of N,N,N',N'-tetramethylethylenediamine (MW: 116, 1.0 mol) and 116 g of distilled water were mixed together in a 1-l four-necked flask fitted with a condenser, a thermometer, a mechanical stirrer and a dropping funnel, while keeping the flask in an ice bath. Thereafter, 208.6 g (2.0 mol) of a 35% aqueous solution of HCl was dropped into the flask through the dropping funnel over a period of about one hour. The reaction mixture was aged for 30 minutes and freed from the water by vacuum distillation with an evaporator to give 185 g of N,N,N',N'-tetramethylethylenediamine hydrochloride. 150 g of this hydrochloride (MW: 189, 0.79 mol), 150 g of dioxane and 73.0 g of ethylene oxide (MW: 44, 1.66 mol) were fed into a 1-l autoclave, which was purged with nitrogen several times. The reaction mixture was heated to 150° C. and aged for 4 hours. After the completion of the reaction, the dioxane was distilled off and the obtained residue was recrystallized from acetone to give 203.2 g of the compound (6) (MW: 277, 0.72 mol).

mixture was aged for one hour and distilled under a reduced pressure to remove the N,N-dimethylformamide. The obtained solid was washed with acetone several times and dried to give 159 g of the compound (7).

MW: 300.6, yield: 85%, purity: 83.1%

Referential Example 8 . . . synthesis of compound (8)

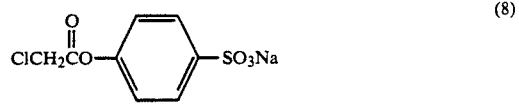
(8)

The same procedure as that of Referential Example 7 was repeated except that 51.9 of monochloroacetyl chloride (MW: 112.9, 0.46 mol) was used instead of the 4-chlorobutyroyl chloride. Thus, the compound (8) was obtained.

amount: 135.1 g, MW: 272.6, yield: 86%, purity: 78.4%

Referential Example 9 . . . synthesis of compound (9)

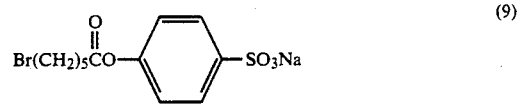
(9)

The same procedure as that of Referential Example 7 was repeated except that 98.2 g of 6-bromocaproyl chloride (MW: 213.5, 0.46 mol) was used instead of the 4-chlorobutyroyl chloride. Thus, the compound (9) was obtained.

amount: 181.7 g, MW: 373.2, yield: 80%, purity: 75.6%

EXAMPLE 1

Synthesis Of Compound (I-a)

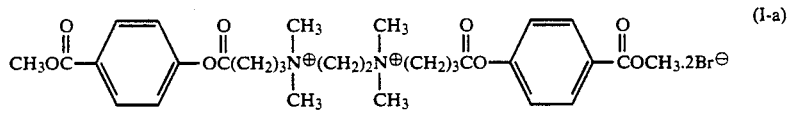
(I-a)

yield: 91%, purity: 98%

Referential Example 7 . . . synthesis of compound (7)

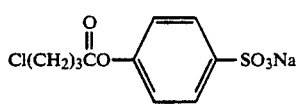
(7)

100 g of disodium p-phenolsulfonate (prepared by neutralizing sodium p-phenolsulfonate with an equimolar amount of caustic soda and dehydrating the neutralization product, MW: 218.2, 0.46 mol) and 300 g of N,N-dimethylformamide were mixed together in a 1-l four-necked flask fitted with a condenser, a mechanical stirrer, a thermometer and a dropping funnel. 64.8 g of 4-chlorobutyroyl chloride (MW: 140.9, 0.46 mol) was dropped into the flask over a period of about 2 hours, while keeping the flask in an ice bath. The reaction 100 g of the compound (2) (MW: 301.3, purity: 93%, 0.31 mol), 300 g of acetone and 17.9 g of N,N,N',N'-tetramethylethylenediamine (MW : 116, 0.15 mol) were mixed together in a 1-l three-necked flask fitted with a condenser, a mechanical stirrer and a thermometer and heated so as to reflux the acetone mildly for about 20 hours to carry out a reaction. The disappearance of the amine was confirmed by titration with a 1/5 N aqueous solution of HCl (indicator: BCG). Thereafter, the reaction mixture was filtered. The obtained crystal was washed with acetone several times and dried to give 62 g of a white crystal (I-a).

MW: 718.5, purity: 86%, yield: 49%

IR (KBr $cm^{-1}$): 1755, 1722, 1608, 1437, 1416, 1377, 1281, 1203, 1161, 1110, 1014, 966, 909, 765

Example 2

Synthesis Of Compound (I-b)

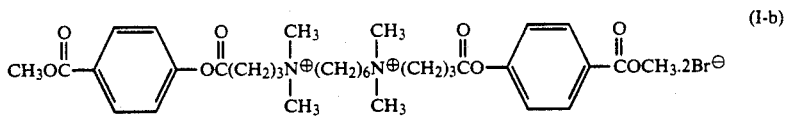

The same procedure as that of Example 1 was repeated except that 25.8 g of N,N,N',N'-tetramethylhexamethylenediamine (MW: 172, 0.15 mol) was used instead of the N,N,N', N'-tetramethylethylenediamine amount: 73.3 g, purity: 84%, yield: 53%

IR (KBr cm$^{-1}$): 2956, 1755, 1722, 1605, 1440, 1377, 1284, 1203, 1161, 1014, 909, 861, 765, 699

EXAMPLE 3

Synthesis Of Compound (I-c)

together in a 1-l four-necked flask fitted with a condenser, a mechanical stirrer, a thermometer and a dropping funnel. 17.4 g of N,N,N',N'-tetramethylethylenediamine (MW: 116, 0.15 mol) was dropped into the flask through the dropping funnel over a period of 5 minutes, while keeping the flask in an ice bath. In this step, the exothermic reaction elevated the reaction temperature by about 15° to 20° C. The reaction mixture was aged for 2 hours. Thereafter, 18.9 g of dimethyl sulfate (MW: 126.1, 0.15 mol) was dropped into the flask through the dropping funnel over a period of about one hour and the reaction was carried out for additional 2 hours. The crystal thus precipitated was

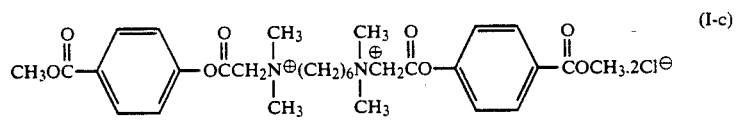

The same procedure as that of Example 2 was repeated except that 77.0 g of the compound (1) (MW: 228.6, purity: 92%, 0.31 mol) was used instead of the compound (2).

amount: 84.0 g, MW: 629.2, purity: 87.6%, yield: 78.0%

IR (KBr cm$^-$): 3010, 2926, 2776, 1776, 1725, 1605, 1503, 1470, 1443, 1413, 1281, 1197, 1161, 1110, 1038, 1008, 996, 900, 861, 798, 777, 732, 687, 507 recovered by filtration, washed with dichloromethane several times and dried to give 54.7 g of a white crystal (I-d).

purity: 87%, yield: 67.4%, MW: 470.7

IR (KBr cm$^{-1}$): 3034, 2950, 2830, 2782, 1773, 1722, 1635, 1608, 1488, 1467, 1437, 1281, 1227, 1164, 1134, 1110, 1059, 1011, 966, 927, 86

EXAMPLE 5

Synthesis Of Compound (I-e)

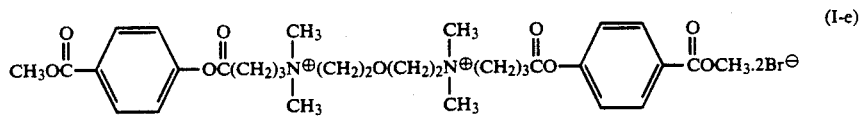

EXAMPLE 4

Synthesis Of Compound (I-d)

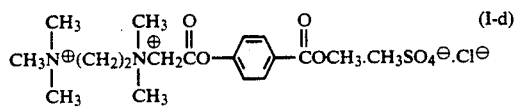

37.3 g of the compound (1) (MW: 228.6, 0.15 mol, purity: 92%) and 150 g of dichloromethane were mixed The same procedure as that of Example 1 was repeated except that 22.8 g of 2,2'-bis(N,N-dimethylamino)diethyl ether (MW: 152.2, 0.15 mol) was used instead of the N,N,N',N'-tetramethylethylenediamine.

amount: 59.4 g, purity: 80%, yield: 42%, MW: 754.8

EXAMPLE 6

Synthesis Of Compound (I-f)

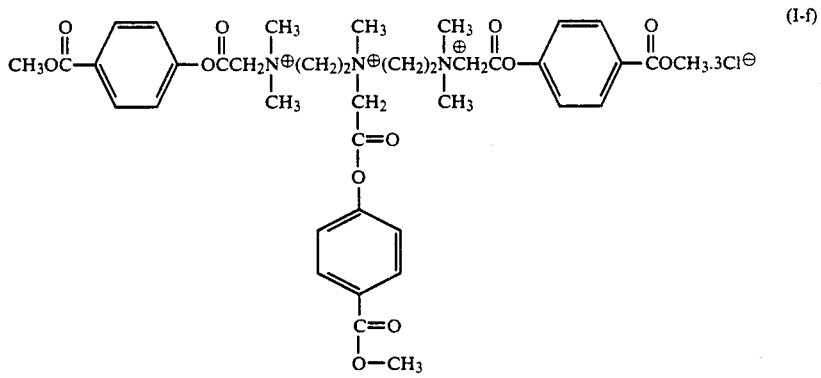

The same procedure as that of Example 3 was repeated except that 38.2 g of N,N,N',N'',N''-diethylenetriamine (KAOLIZER No. 3, a product of Kao Corporation) (MW: 381.9, 0.10 mol) was used instead of the N,N,N',N'-tetramethylhexamethylenediamine.

amount: 41.6 g, purity: 77%, yield: 30%, MW: 1067.7

EXAMPLE 7

Synthesis Of Compound (I-g)

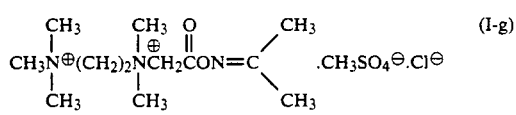

The same procedure as that of Example 4 was repeated except that 22.4 g of the compound (3) (MW: 149.5, purity: 90%, 0.15 mol) was used instead of the compound (1).

amount: 41.1 g, purity: 78%, yield: 55%, MW: 391.6

EXAMPLE 8

Synthesis Of Compound (I-h)

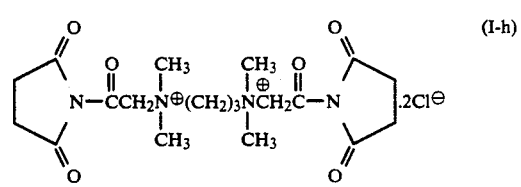

The same procedure that of Example 1 was repeated except that 62.5 g of the compound (4) (MW: 175.4, purity: 87%, 0.13 mol) and 19.5 g of N,N,N',N'-tetramethylpropylenediamine (MW: 130.23, 0.15 mol) were used instead of the compound (2)

amount: 50.4 g, purity: 83%, yield: 53%, MW: 481.0

EXAMPLE 9

Synthesis Of Compound (I-i)

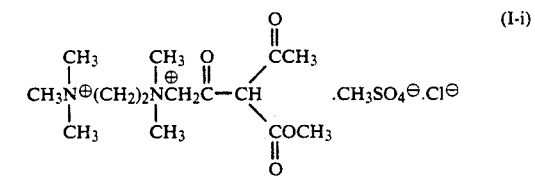

The same procedure as that of Example 4 was repeated except that 44.7 g of the compound (5) (MW: 226.3, plurality: 76%, 0.15 mol) was used instead of the compound (1).

amount: 36.8 g, purity: 86%, yield: 45%, MW: 468.4

EXAMPLE 10

Synthesis Of Compound (I-j)

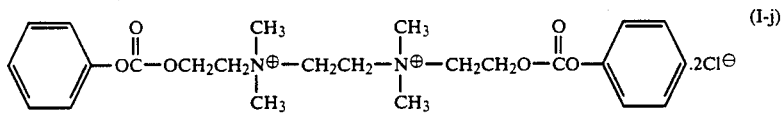

100 g (0.36 mol) of the compound (6), 57.0 g of pyridine (MW: 79.1, 0.72 mol) and 200 g of dimethylformamide were mixed together in a 1-l four-necked flask placed in an ice bath and fitted with a condenser, a thermometer, a mechanical stirrer and a dropping funnel. Thereafter, 112.8 g of phenyl chloroformate (MW: 156.6, 0.72 mol) was dropped into the flask through the dropping funnel over a period of about one hour. The reaction mixture was aged for 2 hours and distilled under a reduced pressure to remove the dimethylformamide. The residue was washed with THF several times to remove pyridine hydrochloride. The residue was recrystallized from acetonitrile to give 158.3 g of the compound (I-j).

MW: 517.2, purity: 95%, yield: 85%

EXAMPLE 11

Synthesis Of Compound (I-k)

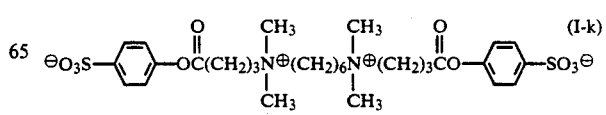

104.9 g (0.29 mol) of the compound (7), 300 g of N,N-dimethylformamide and 25.8 g of N,N,N',N'-tetramethylhexamethylenediamine (MW: 172, 0.15 mol) were mixed together in a 1-l four-necked flask fitted with a condenser, a mechanical stirrer, a thermometer and a dropping funnel and kept at 120° C. for about 12 hours to carry out a reaction. The disappearance of the compound (7) used as the starting material was confirmed by high-performance liquid chromatography. Thereafter, the reaction mixture was distilled under a reduced pressure to remove the N,N-dimethylformamide. The obtained solid was washed with acetone several times and dried to give 69.6 g of the compound (I-k).

MW: 656.2, purity: 82%, yield: 58%

EXAMPLE 12

Synthesis Of Compound (I-l)

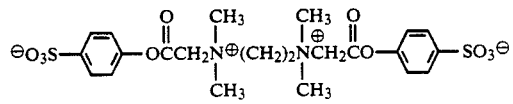

100 g (0.29 mol) of the compound (8), 300 g of N,N-dimethylformamide and 16.9 g of N,N,N',N'-tetramethylethylenediamine (MW: 116, 0.15 mol) were mixed together in a 1-l four-necked flask fitted with a condenser, a mechanical stirrer, a thermometer and a dropping funnel and kept at 80° C. for about 5 hours to carry out a reaction. The disappearance of the compound (8) used as the starting material was confirmed by high-performance liquid chromatography. Thereafter, the reaction mixture was distilled under a reduced pressure to remove the N,N-dimethylformamide. The obtained solid was washed with acetone several times and dried to give 65.3 g of the compound (I-l).

MW: 544.2, purity: 80%, yield: 64%

EXAMPLE 13

Synthesis Of Compound (I-m)

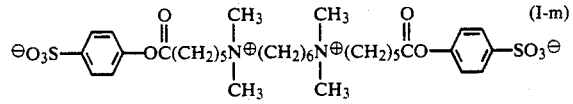

108.2 g (0.29 mol) of the compound (9), 324.6 g of N,N-dimethylformamide and 24.9 g of N,N,N',N'-tetramethylhexamethylenediamine (MW: 172, 0.145 mol) were mixed together in a 1-l four-necked flash fitted with a condenser, a mechanical stirrer, a thermometer and a dropping funnel and kept at 60° C. for about 2 hours to carry out a reaction. The disappearance of the compound (9) used as a starting material was confirmed by high-performance liquid chromatography. Thereafter, the reaction mixture was distilled under a reduced pressure to remove the N,N-dimethylformamide. The obtained solid was washed with acetone several times and dried to give 81.9 g of the compound (I-m).

MW: 712.6, purity: 82%, yield: 65%

TEST EXAMPLE

Determination Of Bleaching Effect

Sodium percarbonate was dissolved in 300 ml of water at 20° C. so as to give an effective oxygen content of 0.05%. The compounds (I-a) to (I-m) and tetraacetylethylenediamine (TAED) for comparison were each added to the obtained solution in an amount as specified in Table 12 to give an equivalent ratio of the compound to the hydrogen peroxide contained in the solution of 1/6. Five tea-stained cloths* prepared by the method which will be described below were dipped in the solution prepared above for 30 minutes, washed with water and dried. The rate of bleaching of the resulting cloth was determined according to the following equation:

rate of bleaching of tea-stained cloth:

$$\text{rate of bleaching (\%)} = \frac{(\text{reflectance after bleaching}) - (\text{reflectance before bleaching})}{(\text{reflectance of white cloth}) - (\text{reflectance before bleaching})} \times 100$$

*tea-stained:
80 g of Nitto black tea (yellow package) was dipped in 3 l of ion-exchanged water, boiled for about 15 minutes, and filtered through a desired bleached cotton cloth. A cotton shirting cloth #2003 was dipped in the obtained filtrate, followed by boiling for about 15 minutes. The boiled liquid was taken off the fire and allowed to stand for about 2 hours. The cloth was dried spontaneously, washed with water until the washings became colorless, dehydrated, pressed and cut into a test piece of 8 cm×8 cm. This test piece was used in the above determination.

The reflectance was determined with an NDR-1001 DP (mfd. by Nippon Denshoku Kogyo) with a filter of 460 nm. The larger the value, the higher the rate of bleaching.

The results are given in Table 1.

TABLE 1

| bleaching activator (wt. %) | Invention | | | | | | | | | | | | | Comp. | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 1 | 2 |
| sodium percarbonate | 82 | 80 | 84 | 78 | 80 | 80 | 79 | 87 | 77 | 88 | 85 | 87 | 84 | 94 | 100 |
| I-a | 18 | | | | | | | | | | | | | | |
| I-b | | 20 | | | | | | | | | | | | | |
| I-c | | | 16 | | | | | | | | | | | | |
| I-d | | | | 22 | | | | | | | | | | | |
| I-e | | | | | 20 | | | | | | | | | | |
| I-f | | | | | | 20 | | | | | | | | | |
| I-g | | | | | | | 21 | | | | | | | | |
| I-h | | | | | | | | 13 | | | | | | | |
| I-i | | | | | | | | | 23 | | | | | | |
| I-j | | | | | | | | | | 12 | | | | | |
| I-k | | | | | | | | | | | 15 | | | | |
| I-l | | | | | | | | | | | | 13 | | | |
| I-m | | | | | | | | | | | | | 16 | | |
| TAED | | | | | | | | | | | | | | | 6 |

TABLE 1-continued

| bleaching activator (wt. %) | Invention | | | | | | | | | | | | | Comp. | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 1 | 2 |
| rate of bleaching (%) | 40 | 40 | 42 | 41 | 40 | 42 | 40 | 41 | 40 | 40 | 42 | 41 | 43 | 23 | 15 |

We claim:

1. A polycationic compound having formula (I):

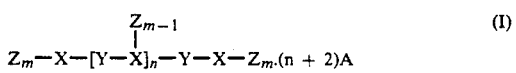

wherein X is $N^+$; Y is an alkylene group having 1 to 9 carbon atoms, which may be substituted with a group selected from the group consisting of a hydroxyl group, a $-(C_2H_4O)_{1-5}-C_2H_4-$ group, and a $-(C_3H_6O)_{1-5}-C_3H_6-$ group, wherein when a plurality of Y groups is present, said Y groups may be the same or different form each other; Z is

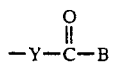

wherein B is

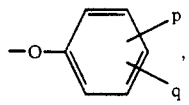

p is H and q is $-SO_3^-$, or Z is an alkyl group having 1 to 20 carbon atoms, or an alkenyl group, each of which may be substituted with a hydroxyl group, a $-(C_2H_4O)_{1-5}-H$ group, or a $-(C_3H_6O)_{1-5}-H$ group, with the proviso that at least one Z group is a

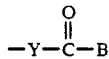

group; m is 3; n is 0; and A is selected from the group consisting of an inorganic and organic anionic group, with the proviso that A is absent when Z and X are combined together to form an inner salt, wherein a plurality of A groups maybe the same or different from each other.

2. The polycationic compound as set forth in claim 1, wherein q is para $-SO_3^-$.

3. The polycationic compound as set forth in claim 2, wherein the compound is selected from the group consisting of

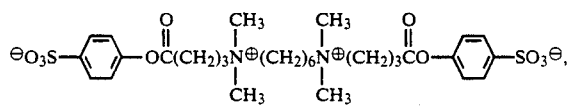

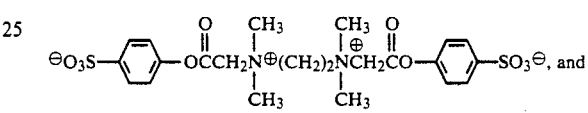, and

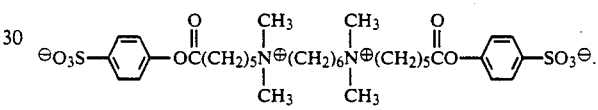

4. The polycationic compound as set forth in claim 1, which

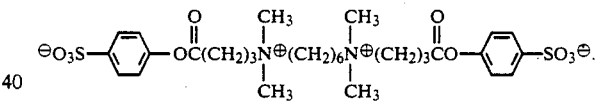

* * * * *